United States Patent [19]

Love

[11] Patent Number: 5,094,823

[45] Date of Patent: Mar. 10, 1992

[54] COMBINATION ACID RECONTACTOR-STORAGE VESSEL

[75] Inventor: Scott D. Love, Bartlesville, Okla.

[73] Assignee: Phillips Petroleum Company, Bartlesville, Okla.

[21] Appl. No.: 535,698

[22] Filed: Jun. 11, 1990

[51] Int. Cl.[5] .................... F28D 1/00; B01J 8/00; B01D 11/04

[52] U.S. Cl. .................... 422/198; 422/224; 422/227; 422/234; 422/256

[58] Field of Search ............... 422/198, 224, 227, 234, 422/256, 111, 106, 216, 223, 235; 208/430

[56] References Cited

U.S. PATENT DOCUMENTS

| | | | |
|---|---|---|---|
| 3,249,650 | 5/1966 | Fenske | 260/683.48 |
| 4,962,268 | 10/1991 | Hovis | 422/140 X |
| 5,021,223 | 6/1991 | Hovis | 422/198 |

OTHER PUBLICATIONS

Hydrofluoric Acid Alkylation, Phillips Petroleum Company, 1946, pp. 30–31, 34–35, 23.

Primary Examiner—Robert J. Warden
Assistant Examiner—Long V. Le
Attorney, Agent, or Firm—Charles W. Stewart

[57] ABSTRACT

An improved method and apparatus for the safe handling of alkylation catalyst. The method and apparatus comprises a process vessel which serves a dual function of storing alkylation catalyst and of recontacting alkylation hydrocarbon product with alkylation catalyst. Alkylate product is passed through an eductor-mixer device which intimately mixes alkylate with catalyst. This mixture flows into the dual function recontacting vessel where a phase separation of the catalyst and alkylation hydrocarbon product takes place. Conduits are provided to connect the process reactor, cooling heat exchanger, settler, and interconnecting piping so as to allow the quick release of pressure from the combination storage-recontacting vessel and subsequent draining of catalyst into the vessel by use of gravitational force. The method and apparatus consists of a physical arrangement and use of alkylation process equipment in a manner which allows the use of a single vessel for both storage of alkylation catalyst and recontacting of alkylation hydrocarbon product. The apparatus and method is a safety feature which allows the transfer by draining of catalyst from the alkylation process vessels into the storage vessel by the sole use of gravitational energy motive force.

6 Claims, 1 Drawing Sheet

COMBINATION ACID RECONTACTOR-STORAGE VESSEL

This invention relates to the process of reacting isoparaffin and olefin compounds in the presence of an acid catalyst to form high octane gasoline alkylate product. Another aspect of this invention involves the recontacting of the alkylate reaction product, containing a quantity of organic fluoride reaction by-products, with relatively pure hydrogen fluoride catalyst in order to further convert the alkyl fluoride compounds to additional alkylate thereby increasing the process alkylate yield. A further aspect of this invention involves the arrangement of process equipment which allows for the use of a single vessel to serve a dual function of storing catalyst and of recontacting alkylate with alkylation catalyst, and further allows the draining of catalyst contained in certain process equipment by the sole use of gravitational motive force into a safe haven vessel.

In an alkylation process, high octane gasoline is produced by reacting in the presence of catalyst, preferably hydrogen fluoride, isoparaffins with olefins. Some of the alkylation reaction by-products are alkyl fluorides that are contaminants to the hydrocarbon products produced from an alkylation unit and, therefore, they must be removed. Various means have been used to remove alkyl fluorides one of which is the recontacting of the alkyl fluoride with high purity hydrogen fluoride to convert the alkyl fluoride compounds into additional high octane alkylate. This recontacting process is preferable over other alternative means of removing alkyl fluoride compounds in that a greater yield of high octane alkylate is produced and catalyst consumption is lowered. In a typical alkylation process unit, there is often provided a section in which the separated hydrocarbon phase of the reactor effluent is passed through an eductor device which draws hydrogen fluoride into the secondary inlet of the device and which mixes the two phases. The recontacted mixture passes to an acid recontacting vessel where the hydrocarbon phase and catalyst phase separate. During this recontacting step, the organic fluorides react to produce additional alkylate and release additional hydrogen fluoride.

Another concern with the alkylation process is the safe handling, transport, and storage of the alkylation catalyst. As is typically done, a catalyst storage vessel is provided where make-up catalyst is stored and in which the inventory of catalyst contained in the alkylation process may be inventoried when required. In emergency situations, there must be a means for quickly and safely transferring the process catalyst to safe containment within the storage vessel. Because of the hazardous nature of alkylation catalyst, any reduction in the number of separately contained volumes of catalyst held within the process can result in an improvement in operating safety of an alkylation process.

Accordingly, an object of this invention is to provide an improved alkylation process.

Another object of this invention is to improve the operating safety of an alkylation process.

A further object of this invention is to provide a process for removing alkyl fluoride compounds from alkylate product.

A still further object of this invention is to provide alkylation process equipment which eliminates a separate inventory volume of alkylation catalyst while providing means for safely storing alkylation catalyst.

Yet another object of this invention is to provide a process for removing alkyl fluorides within a vessel which serves a dual function as a storage vessel and as a recontacting vessel.

According to this invention, an apparatus is provided which allows for the incremental reduction of organic fluorides from alkylate product by using a process vessel which serves a dual function as a recontacting vessel and as a vessel for storage of alkylation catalyst. With this invention, one vessel in the alkylation process is eliminated which reduces certain capital costs associated with an alkylation process. Moreover, a separate inventory source of alkylation catalyst is eliminated from the process which results in an improvement in the operating safety of an alkylation unit.

Other objects, aspects, and features of the present invention will be evident from the following detailed description of the invention, the claims and the drawing in which:

BRIEF DESCRIPTION OF THE DRAWING

Referring to FIG. 1, a hydrocarbon feed mixture of isoparaffins and olefins is introduced into reactor 10 of the alkylation process through line 12. At the point of introduction of the hydrocarbon feed, cooled alkylation catalyst exiting heat exchanger or acid cooler 14 and entering reactor 10 via conduit 16 is intimately mixed with the incoming hydrocarbon feed in reactor 10. Operating conditions within reactor 10 of an alkylation process are well known in the art and are not repeated here.

Figure 1:
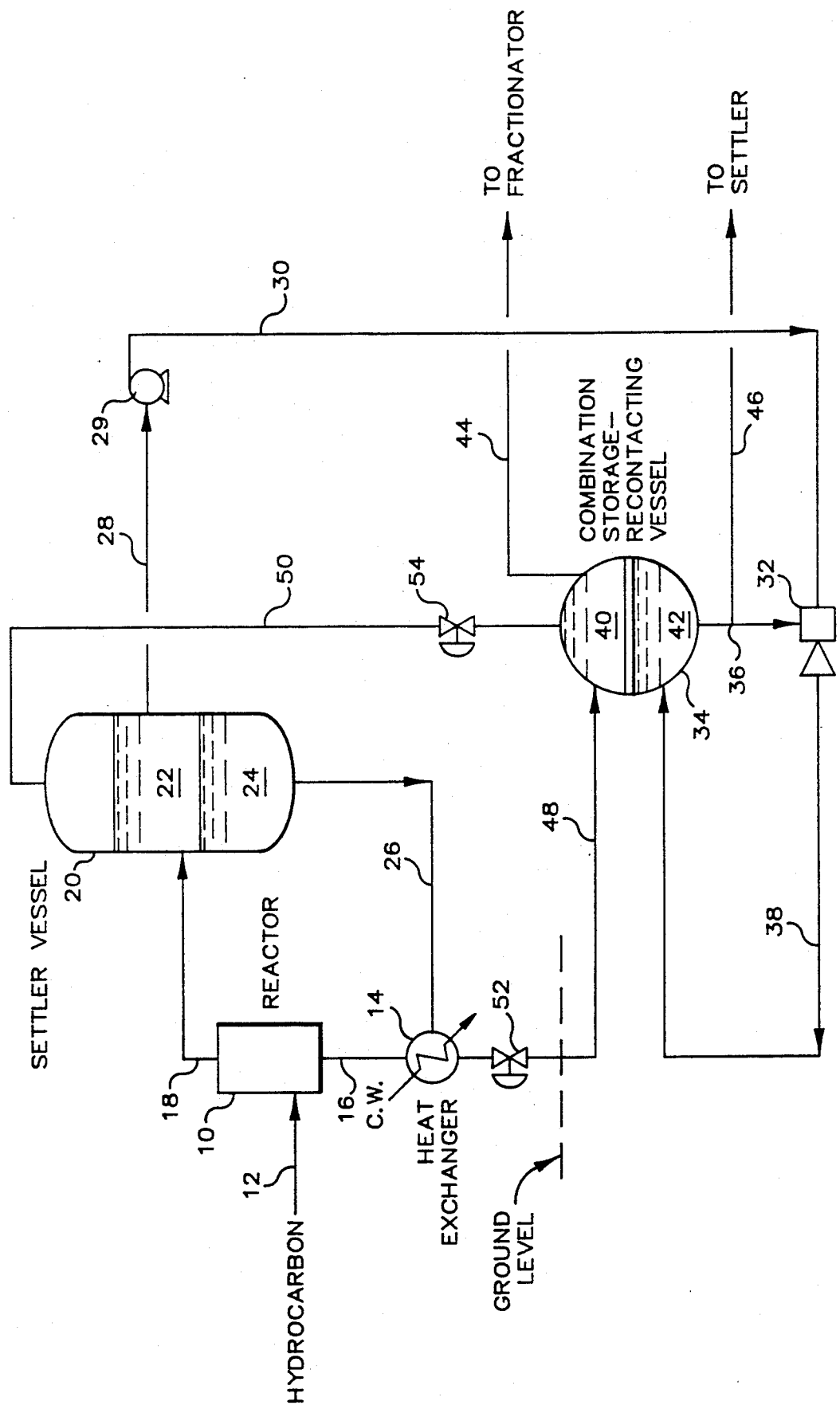
FIG. 1 is a schematic diagram illustrating a preferred embodiment of the present invention.

Effluent from reactor 10 is discharged via conduit 18 into settler vessel 20 wherein a phase separation between the hydrocarbon phase 22 and the catalyst phase 24 takes place with catalyst phase 24 settling to the lower portion of settler vessel 20 and with the hydrocarbon phase 22 forming on top of the catalyst phase 24 due to the immiscibility and density difference between the two phases. The settled out catalyst phase 24 returns to heat exchanger 14 through conduit 26 providing a closed circuit for the circulation of catalyst in the alkylation process.

The hydrocarbon phase 22 from settler vessel 20 is withdrawn via line 28 into the inlet side of pump or other suitable mechanical device 29 which is used to impart velocity and pressure energy head, with the pressure energy head generally ranging between about 100 psi and about 300 psi, to the alkylation product. The discharge of said pump 29 passes to the primary inlet of an eductor-mixing device 32 by way of line 30. The secondary inlet to eductor-mixing device 32 is fed with alkylation catalyst drawn from combination storage-recontacting vessel 34 by way of line 36. The eductor-mixing device 32 provides for the mixing of organic fluoride-containing alkylate product with hydrogen fluoride catalyst to yield additional alkylate and to release additional hydrogen fluoride.

The outlet stream from eductor-mixing device 32 passes by way of line 38 to combination storage-recontacting vessel 34 where a separation of the hydrocarbon phase 40, which may also be called the alkylate product phase, and catalyst phase 42 takes place. Combination storage-recontacting vessel 34 is physically located at a relative elevation below those of heat exchanger 14, reactor 10, settler vessel 20 and the interconnecting piping. This elevation difference allows for the draining, when circumstances require, of the catalyst inventory contained in the process equipment into combination storage-recontacting vessel 34 by use of gravitational motive force. The alkylate product phase 40 which has been separated from the catalyst phase 42 in combination storage-recontacting vessel 34 is withdrawn from vessel 34 through line 44 and charged to the fractionation section of the alkylation process (not shown). Catalyst is preferably removed from vessel 34 through line 46 at a rate of flow which approximates the rate of flow of incoming catalyst which is undissolved in the hydrocarbon phase effluent stream flowing through line 28 plus the catalyst produced in the recontacting reaction.

Storage-recontacting vessel 34 is further interconnected to the alkylation process by lines 48 and 50. Line 48 connects heat exchanger 14 with vessel 34 in a manner which allows the gravitational draining of catalyst from the process sections comprising heat exchanger 14, reactor 10, settler vessel 20, and interconnecting piping when pressure is released from vessel 34 via line 50 to settler vessel 20. Placed at a relative elevation above combination storage-recontacting vessel 34 are control values 52 and 54 inserted in lines 48 and 50, respectively. When the alkylation process is operating under normal conditions, these valves are placed in the closed position and are generally only placed in the open position when catalyst is being transferred from the process.

Other objects, aspects, and features of the present invention will be evident from the following examples.

In the operation of this invention, hydrocarbon reaction product is withdrawn from the settler vessel 20 of an alkylation process via conduits 28, 30 and pump 29 and it is recontacted with hydrogen fluoride catalyst in the eductor-mixing device 32, conduit 38 and storage-recontacting vessel 34 to form an admixture. In this recontacting step, reactions take place where certain quantities of alkyl fluoride that are present in the alkylate product are reacted to yield an additional quantity of alkylate and to recombine additional hydrogen fluoride catalyst. This recontacting step gives the benefit of increasing the yield of high octane alkylate and the benefit of reducing the amount of acid catalyst consumed in operating the process. Both of these benefits improve the economics of operating an alkylation process. Table I shows the incremental benefits achieved by using the combination recontactor-storage vessel, and it shows typical operating conditions, flows and compositions.

TABLE I

| OPERATING CONDITIONS AND FLOWS (Calculated) | |
|---|---|
| Settler Vessel Effluent | |
| Pressure, psig | 120 |
| Temperature, °F. | 90 |
| Hydrocarbon flow rate, BPD | 38,000 |
| HF flow, BPD | 300 |
| lb/day | 100,300 |
| Organic Fluorides, ppm (wt) | 300 |
| lb/day | 2,640 |
| Pump | |
| Pressure differential, psi | 250 |
| Combination Recontactor-Storage Vessel | |
| Pressure, psig | 370 |
| Temperature, °F. | 90 |
| Hydrocarbon Charge to Fractionation | |
| hydrocarbon flow rate, BPD | 38,000 |
| organic fluorides, ppm (wt) | 200 |

TABLE I-continued

| OPERATING CONDITIONS AND FLOWS (Calculated) | |
|---|---|
| lb/day | 1760 |
| HF to Settler from fractionation section and combination storage-recontacting vessel | |
| flow, BPD | 300.7 |
| lb/day | 100,530 |
| Additional alkylate produced from alkylfluorides | |
| BPD | 5 |
| HF Savings | |
| lb/day | 230 |
| BPD | 0.7 |
| Equipment Savings | |
| elimination of one process vessel | |

The admixture of hydrogen fluoride catalyst and alkylate passes to the vessel 34 which serves a combined function as a recontacting vessel for reacting and separating the catalyst and hydrocarbon phases of the mixture generated from the eductor mixer 32 and as a catalyst storage vessel. This combined storage-recontactor vessel 34 is preferably placed at a physical location having a relative elevation below those of the reaction, settling, and cooling sections 10, 20 and 14, respectively, of the alkylation process in a manner that allows for the quick draining by use of gravitational motive force of catalyst contained within the process equipment. This particular embodiment can further be expanded to where the combined storage-recontacting vessel is placed under ground, as illustrated in FIG. 1, leaving the remaining process equipment comprising the reaction, settling, and cooling sections above ground.

Under this specific embodiment, the underground vessel provides several safety benefits in the design and operation of an alkylation unit. One safety benefit involves the lowering of the vertical elevation of the process equipment, such as the settler vessel 20 and acid cooler 14 below an elevation where these pieces of equipment normally reside. By lowering the vertical elevation of this equipment, any catalyst leaks or spills which might originate from the process equipment, although highly unlikely, would occur closer to ground level which reduces the area over which such a spill or leak may spread. A further safety benefit from this equipment arrangement is that it provides a means for quick draining of the alkylation catalyst to safe storage below ground by use of gravitational force in emergency situations. Moreover, with the underground location, chemical neutralization safety equipment may be designed for the more effective control of any potential catalyst spills or leaks.

Reasonable variations and modifications are possible within the scope of the foregoing disclosure, drawing, and appended claims.

That which is claimed is:

1. In an alkylation apparatus containing an inventory of catalyst wherein hydrocarbon feed mixture and alkylation catalyst are reacted to produce an effluent comprising a hydrocarbon phase and a catalyst phase of the type which includes:
    heat exchanger means, having a catalyst inlet, a catalyst outlet and a drain outlet, for cooling catalyst passing therethrough;
    reactor means, having an upper end portion and a lower end portion, for reacting hydrocarbon feedstock and catalyst to produce a reaction effluent comprising a hydrocarbon phase and a catalyst phase;

first conduit means in fluid flow communication between the catalyst outlet of said heat exchanger means and the lower end portion of said reactor means for conducting cooled catalyst from said heat exchanger means to said reactor means;

second conduit means in fluid flow communication between a source of hydrocarbon feedstock and the lower end portion of said reactor means for conducting said hydrocarbon feedstock to said reactor means;

settler vessel means, having an upper end portion, a lower end portion and a medial portion, and located at a relative elevation above said heat exchanger means, for separating the reaction effluent from said reactor means into a catalyst phase in the lower end portion of said settler vessel and a hydrocarbon phase above said catalyst phase in said settler vessel;

third conduit means in fluid flow communication between the upper end portion of said reactor means and said settler vessel means for conducting reaction effluent from said reactor means to said settler vessel means; and fourth conduit means in fluid flow communication between the lower end portion of said settler vessel means and the catalyst inlet of said heat exchanger means for conducting catalyst from the catalyst phase in the lower end portion of said settler vessel to said heat exchanger means;

the improvement comprising:

combination storage-recontacting vessel means, having an upper end portion, a lower end portion and a medial portion, and located at a relative elevation below said heat exchanger means, and of sufficient size to store the entire catalyst inventory contained in said alkylation apparatus, for storing at least a portion of said catalyst inventory and for contacting hydrocarbon phase from said settler vessel means and catalyst from said heat exchanger means;

fifth conduit means in fluid flow communication between the drain outlet of said heat exchanger means and said combination storage-recontacting vessel means for selectively conducting catalyst from said heat exchanger means to said combination storage-recontacting vessel means;

sixth conduit means in fluid flow communication between said settler vessel means and said combination storage-recontacting vessel means for selectively equalizing the pressures therein;

seventh conduit means in fluid flow communication between said settler vessel means and said combination storage-recontacting vessel means for conducting hydrocarbons from the hydrocarbon phase in said settler vessel means to said combination storage-recontacting vessel means;

eighth conduit means, having a first end portion and a second end portion, with the first end portion thereof in fluid flow communication with the lower end portion of said combination storage-recontacting vessel means; and eductor means interposed in said seventh conduit means and in fluid flow communication with the second end portion of said eighth conduit means for withdrawing catalyst from said combination storage-recontacting vessel means and for contacting hydrocarbon from said settler vessel means and catalyst from said combination storage-recontacting vessel means and forwarding said thus contacted hydrocarbon and catalyst through said seventh conduit means to said combination storage-recontacting vessel means.

2. An apparatus as recited in claim 1, further comprising:

first valve means interposed in said fifth conduit means for blocking passage of liquid through said fifth conduit means, and, alternatively, allowing passage of liquid through said fifth conduit means.

3. An apparatus as recited in claim 2, further comprising:

second valve means interposed in said sixth conduit means for blocking passage of fluid through said sixth conduit means, and, alternatively, allowing passage of liquid through said sixth conduit means.

4. An apparatus as recited in claim 3, further comprising:

pumping means interposed in said seventh conduit means for imparting head to hydrocarbon withdrawn from said settler vessel means and forwarding said hydrocarbon to the inlet of said eductor means.

5. An apparatus as recited in claim 1, wherein:

said combination storage-recontacting vessel means is located at a relative elevation below said heat exchanger means.

6. An apparatus as recited in claim 5, wherein:

said combination storage-recontacting vessel means is located below ground level.

* * * * *

UNITED STATES PATENT AND TRADEMARK OFFICE
CERTIFICATE OF CORRECTION

PATENT NO. : 5,094,823
DATED : March 10, 1992
INVENTOR(S) : Scott D. Love and Stone P. Washer It is certified that error appears in the above-identified patent and that said Letters Patent is hereby corrected as shown below:

On the title page of the patent under "INVENTORS", please add the following co-inventor ---Stone P. Washer, Bartlesville, Okla.---

Signed and Sealed this

Fourth Day of May, 1993

Attest:

MICHAEL K. KIRK

Attesting Officer

Acting Commissioner of Patents and Trademarks